US012708348B2

(12) United States Patent
Matsumoto et al.

(10) Patent No.: US 12,708,348 B2
(45) Date of Patent: Aug. 18, 2026

(54) ULTRASOUND DIAGNOSTIC APPARATUS

(71) Applicant: FUJIFILM Healthcare Corporation, Chiba (JP)

(72) Inventors: Tsuyoshi Matsumoto, Tokyo (JP); Tomoki Inoue, Tokyo (JP); Tomohiko Tanaka, Tokyo (JP); Nobuhiko Fujii, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 93 days.

(21) Appl. No.: 18/774,876

(22) Filed: Jul. 16, 2024

(65) Prior Publication Data

US 2025/0040911 A1 Feb. 6, 2025

(30) Foreign Application Priority Data

Aug. 2, 2023 (JP) ................................ 2023-126323

(51) Int. Cl.
*A61B 8/00* (2006.01)

(52) U.S. Cl.
CPC ............ *A61B 8/488* (2013.01); *A61B 8/5207* (2013.01); *A61B 8/5223* (2013.01)

(58) Field of Classification Search
CPC ...... A61B 8/488; A61B 8/5207; A61B 8/5223
See application file for complete search history.

(56) References Cited

U.S. PATENT DOCUMENTS

2009/0088640 A1* 4/2009 Park .................... G06F 18/2148 707/E17.046
2017/0086792 A1* 3/2017 Chono .................... A61B 8/06
2018/0146956 A1 5/2018 Imai
2020/0226757 A1* 7/2020 Hare, II .................. G06N 3/09
2020/0345324 A1 11/2020 Matsumoto et al.

FOREIGN PATENT DOCUMENTS

JP 2018082794 5/2018
WO 2017033503 3/2017
WO 2019150715 8/2019
WO WO-2021161683 A1 * 8/2021 ............ A61B 8/488

* cited by examiner

*Primary Examiner* — Chao Sheng
(74) *Attorney, Agent, or Firm* — JCIPRNET

(57) ABSTRACT

An information processing unit included in an ultrasound diagnostic apparatus executes a process of generating a B-mode image based on transmission of an ultrasonic wave to a subject and reception of the ultrasonic wave reflected by the subject, a process of generating a Doppler waveform image based on transmission of an ultrasonic wave to the subject and reception of the ultrasonic wave reflected by the subject, a process of recognizing a Doppler observation target on the B-mode image, and a process of generating an evaluation value for the Doppler waveform image based on a reference Doppler waveform image corresponding to the Doppler observation target and the Doppler waveform image.

11 Claims, 6 Drawing Sheets

Figure 1:
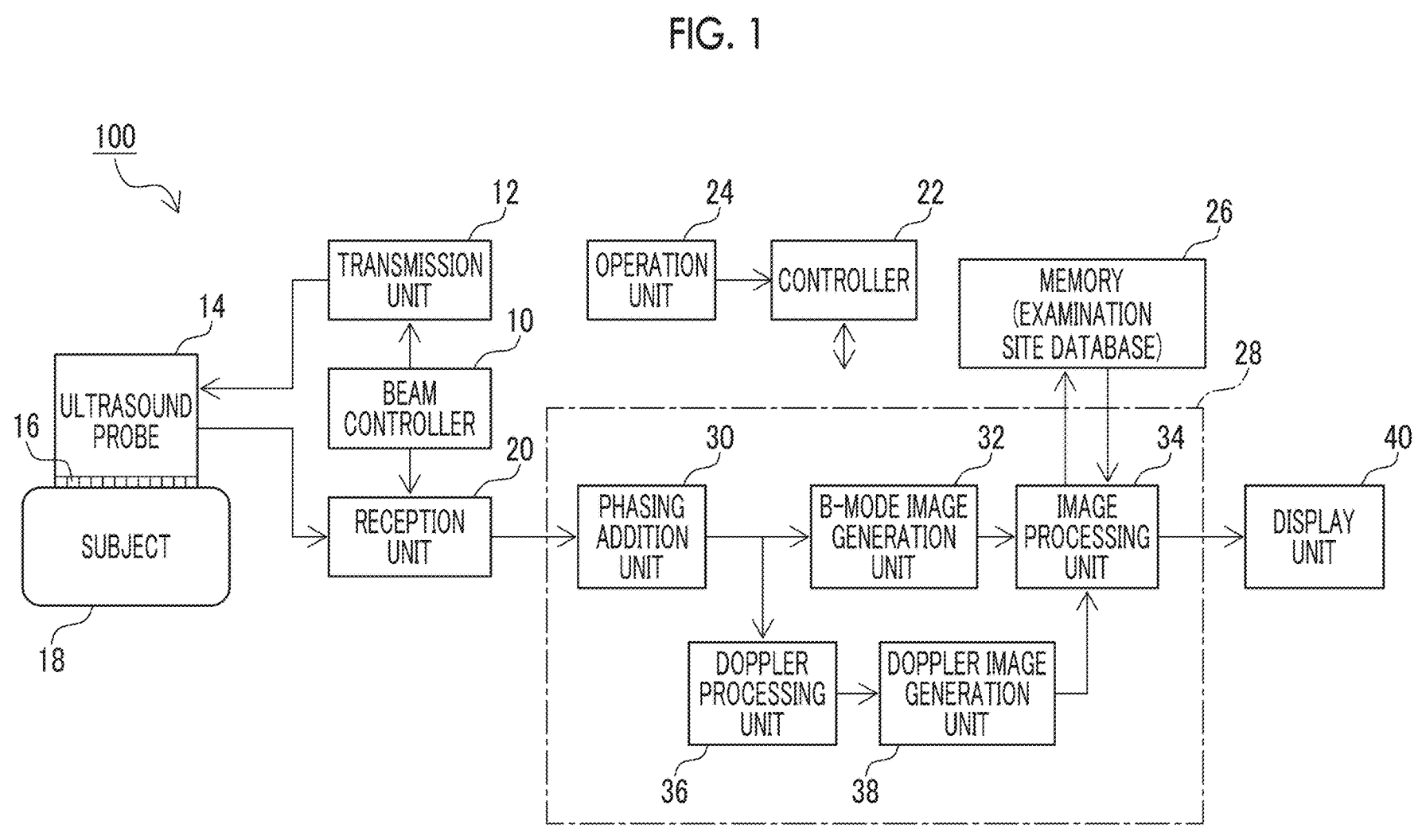

ULTRASOUND PROBE 14

16

SUBJECT 18

TRANSMISSION UNIT 12

BEAM CONTROLLER 10

RECEPTION UNIT 20

OPERATION UNIT 24

CONTROLLER 22

MEMORY (EXAMINATION SITE DATABASE) 26

28

PHASING ADDITION UNIT 30

B-MODE IMAGE GENERATION UNIT 32

IMAGE PROCESSING UNIT 34

DOPPLER PROCESSING UNIT 36

DOPPLER IMAGE GENERATION UNIT 38

DISPLAY UNIT 40

ULTRASOUND DIAGNOSTIC APPARATUS

CROSS-REFERENCE TO RELATED APPLICATION

This application claims the priority benefit of Japan application serial no. 2023-126323, filed on Aug. 2, 2023. The entirety of the above-mentioned patent application is hereby incorporated by reference herein and made a part of this specification.

BACKGROUND OF THE INVENTION

1. Field of the Invention

The present disclosure relates to an ultrasound diagnostic apparatus, and particularly relates to an apparatus that generates a B-mode image and a Doppler waveform image.

2. Description of the Related Art

An ultrasound diagnostic apparatus is widely used. The ultrasound diagnostic apparatus transmits ultrasonic waves from an ultrasound probe to a subject, and generates a B-mode image showing a tomographic of the subject and a Doppler waveform image showing a blood flow velocity based on a reception signal obtained by receiving the ultrasonic waves reflected by the subject with the ultrasound probe. As shown in JP2018-082794A, there is an ultrasound diagnostic apparatus that displays a B-mode image of a subject and displays a Doppler waveform image for a blood vessel displayed in the B-mode image. In addition, as shown in WO2019/150715A and WO2017/033503A, there is an ultrasound diagnostic apparatus that discriminates a site indicated by a B-mode image of a subject based on the B-mode image.

SUMMARY OF THE INVENTION

In the ultrasound diagnostic apparatus, in a case where a position or a posture of the ultrasound probe is not appropriate, an appropriate Doppler waveform image may not be displayed. In addition, since an appropriate position or posture of the ultrasound probe differs depending on a site as an observation target, it may be difficult for a user to perform an operation of displaying an appropriate Doppler waveform image.

An object of the present disclosure is to facilitate a process of displaying an appropriate Doppler waveform image in an ultrasound diagnostic apparatus.

An ultrasound diagnostic apparatus according to an aspect of the present disclosure comprises: an information processing unit that executes a process of generating a B-mode image based on transmission of an ultrasonic wave to a subject and reception of the ultrasonic wave reflected by the subject, a process of recognizing a Doppler observation target in the subject on the B-mode image, a process of generating a Doppler waveform image for the Doppler observation target based on transmission of an ultrasonic wave to the subject and reception of the ultrasonic wave reflected by the subject, and a process of generating an evaluation value for the Doppler waveform image based on a reference Doppler waveform image corresponding to the Doppler observation target and the Doppler waveform image.

In one embodiment, the information processing unit constructs a machine learning model that specifies an examination site as the Doppler observation target in response to being given the B-mode image, and outputs the evaluation value for the reference Doppler waveform image in response to being given information specifying the examination site and the Doppler waveform image.

In one embodiment, the information processing unit executes a process of recognizing one of a plurality of types of examination sites as the Doppler observation target by referring to the B-mode image and an examination site database in which a reference B-mode image is associated with each of the plurality of types of examination sites.

In one embodiment, the information processing unit obtains a degree of approximation between the B-mode image and the reference B-mode image for the plurality of types of examination sites, specifies reference B-mode image data having a greatest degree of approximation, and recognizes the examination site associated with the specified reference B-mode image data as the Doppler observation target.

In one embodiment, the information processing unit constructs a disease determination model that outputs a type of a disease, a disease possibility evaluation value for the disease, and disease Doppler waveform image data in response to being given information specifying an examination site and Doppler waveform image data, and sets the Doppler observation target as the examination site.

In one embodiment, the information processing unit executes a process of indicating a possibility that a disease is recognized in the Doppler observation target based on a disease Doppler waveform image showing a Doppler waveform image in a case where the disease is recognized in the Doppler observation target and the Doppler waveform image.

In one embodiment, the information processing unit executes a process of displaying the evaluation value, and executes a process of adjusting an operation parameter of the ultrasound diagnostic apparatus based on the B-mode image or the Doppler waveform image, in response to an operation of a user when the evaluation value is displayed.

In one embodiment, the information processing unit executes a process of adjusting an operation parameter of the ultrasound diagnostic apparatus based on the B-mode image or the Doppler waveform image, in a case where the evaluation value is less than a predetermined reference value.

In one embodiment, the information processing unit constructs a detail evaluation model that outputs a detail included in an examination site, the reference Doppler waveform image for the detail, and the evaluation value in response to being given information specifying the examination site and the Doppler waveform image, and sets the Doppler observation target for which the evaluation value has been previously generated as the examination site in the detail evaluation model.

In one embodiment, the information processing unit executes a process of recognizing a detail included in the Doppler observation target for which the evaluation value has been previously generated based on the Doppler waveform image and the reference Doppler waveform image for a detail included in an examination site, and the process of generating the evaluation value includes a process of generating the evaluation value based on the Doppler waveform image and the reference Doppler waveform image corresponding to the detail.

In one embodiment, the information processing unit executes a process of providing a user with an instruction for an operation of an ultrasound probe through a man-machine interface based on the evaluation value.

According to the present disclosure, it is possible to facilitate a process of displaying an appropriate Doppler waveform image in an ultrasound diagnostic apparatus.

BRIEF DESCRIPTION OF THE DRAWINGS

FIG. 1 is a diagram showing a configuration of an ultrasound diagnostic apparatus according to an embodiment of the present disclosure.

DESCRIPTION OF THE PREFERRED EMBODIMENTS

Figure 2:
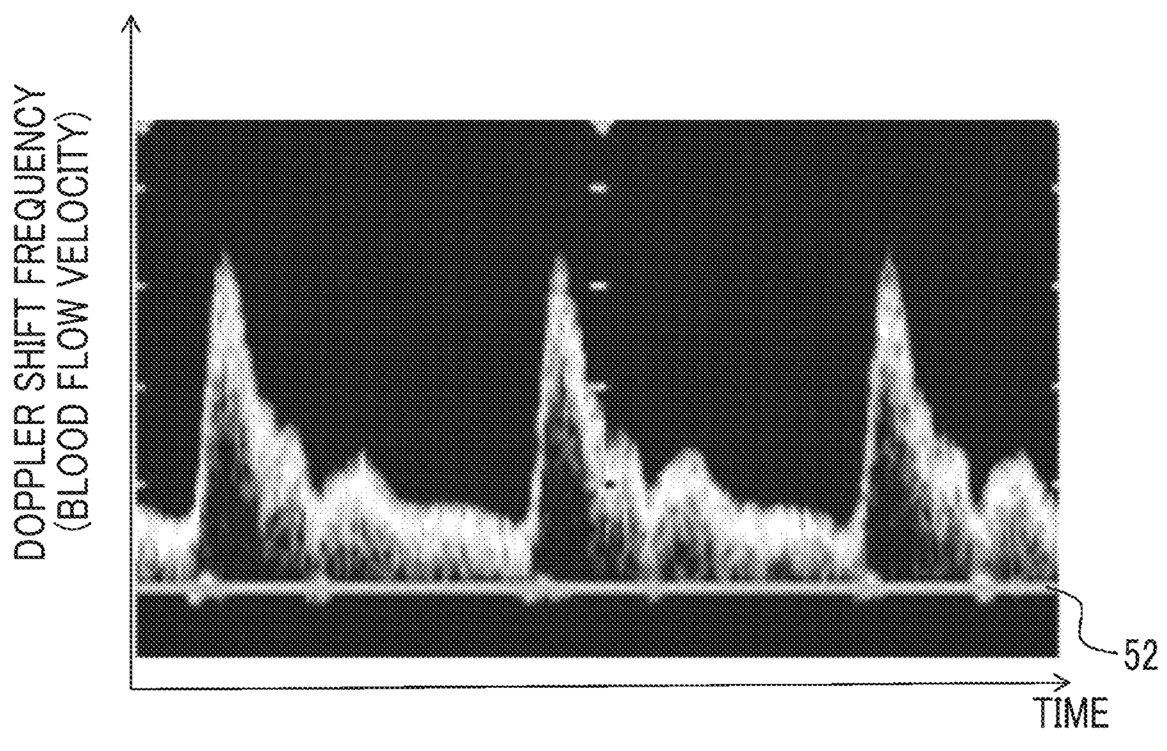
FIG. 2 is a diagram showing an example of a Doppler waveform image.

Each embodiment of the present disclosure will be described with reference to each drawing. The same components shown in a plurality of drawings are designated by the same reference numerals, and the description thereof will not be repeated. In addition, in the present specification, the term "A image" in which the term "image" is continued after a certain specific name "A" means an image indicated by "A image data". In addition, the expression "to generate A image data" may be expressed in a simplified manner as "to generate A image".

FIG. 1 shows a configuration of an ultrasound diagnostic apparatus 100 according to an embodiment of the present disclosure. The ultrasound diagnostic apparatus 100 comprises a beam controller 10, a transmission unit 12, an ultrasound probe 14, a reception unit 20, a controller 22, an operation unit 24, a memory 26, an information processing unit 28, and a display unit 40. The information processing unit 28 may be configured by one or a plurality of processors that execute a program to realize functions of a phasing addition unit 30, a B-mode image generation unit 32, an image processing unit 34, a Doppler processing unit 36, and a Doppler image generation unit 38. The controller 22 performs overall control of the ultrasound diagnostic apparatus 100. The operation unit 24 includes a keyboard, a mouse, a lever, a button, and the like, and outputs information related to an operation of a user to the controller 22. The operation unit 24 may include a touch panel on a display screen of the display unit 40. The controller 22 may control the ultrasound diagnostic apparatus 100 in response to an operation on the operation unit 24.

A description of an outline of an operation of the ultrasound diagnostic apparatus 100 will be made. The ultrasound diagnostic apparatus 100 transmits ultrasonic waves from the ultrasound probe 14 to a subject 18 and receives the ultrasonic waves reflected by the subject 18 with the ultrasound probe 14. The ultrasound diagnostic apparatus 100 executes each measurement in a B-mode and a Doppler mode. In a B-mode operation, the ultrasound diagnostic apparatus 100 generates a B-mode image based on the ultrasonic waves received from the subject 18, and displays the B-mode image on the display unit 40. In a Doppler mode operation, the ultrasound diagnostic apparatus 100 generates a Doppler waveform image in the subject 18 based on a Doppler shift frequency of the ultrasonic waves received from the subject 18, and displays the Doppler waveform image on the display unit 40. Only one of the B-mode operation or the Doppler mode operation may be executed, or measurements in these two modes may be performed in time division.

A specific configuration of the ultrasound diagnostic apparatus 100 and specific processes executed by the ultrasound diagnostic apparatus 100 will be described. The ultrasound probe 14 is in a state of being in contact with a surface of the subject 18. The ultrasound probe 14 comprises a plurality of transducer elements 16. The transmission unit 12 outputs a transmission signal to each of the transducer elements 16 of the ultrasound probe 14 based on the control by the beam controller 10. As a result, the ultrasonic waves are transmitted from the ultrasound probe 14. The beam controller 10 controls the transmission unit 12 to form a transmission beam in the ultrasound probe 14 and scans the subject 18 with the transmission beam. That is, the transmission unit 12 adjusts a delay time or a level of each transmission signal in accordance with the control of the beam controller 10, forms a transmission beam in the ultrasound probe 14, and scans the subject 18 with the transmission beam.

In a case where the ultrasonic waves reflected in the subject 18 are received by each transducer element 16 of the ultrasound probe 14, each transducer element 16 outputs an electric signal corresponding to the received ultrasonic waves to the reception unit 20. The reception unit 20 performs processing such as amplification, detection, and frequency band limitation on the reception signal output from each transducer element 16 in accordance with the control of the beam controller 10, and outputs the processed reception signal to the phasing addition unit 30.

The phasing addition unit 30 performs phasing addition of a plurality of the reception signals output from the reception unit 20 for the plurality of transducer elements 16 to generate a phase-adjusted reception signal. As a result, a phase-adjusted reception signal obtained through phase adjustment and addition such that the reception signals based on the ultrasonic waves received from a specific direction strengthen each other is generated, and a reception beam is formed in the specific direction. The phasing addition unit 30 outputs the phase-adjusted reception signal to the B-mode image generation unit 32 during the B-mode operation, and outputs the phase-adjusted reception signal to the Doppler processing unit 36 during the Doppler mode operation.

The B-mode operation will be described. The phasing addition unit 30 generates each phase-adjusted reception signal based on the ultrasonic wave received from each direction of the reception beam scanned in the subject 18, and outputs the phase-adjusted reception signal to the B-mode image generation unit 32. The B-mode image generation unit 32 generates B-mode image data based on the phase-adjusted reception signal obtained in each reception beam direction, and outputs the B-mode image data to the image processing unit 34. The B-mode image data based on one scan of the transmission beam and the reception beam is image data for one frame, and corresponds to one B-mode image.

The beam controller 10, the transmission unit 12, the ultrasound probe 14, the reception unit 20, the phasing addition unit 30, and the B-mode image generation unit 32 generate the B-mode image data one after another in association with repetitive scan of the transmission beam and the reception beam, and output each B-mode image data to the image processing unit 34. The image processing unit 34 generates a video signal for displaying the B-mode image based on the B-mode image data, and outputs the video signal to the display unit 40. The display unit 40 displays the B-mode image based on the video signal.

Next, the Doppler mode operation will be described. The Doppler mode includes a pulse wave Doppler mode (PW Doppler mode) in which an ultrasonic pulse is transmitted at a repetition frequency PRF and a continuous wave Doppler mode (CW Doppler mode) in which the ultrasonic wave is continuously transmitted. Whether to operate in the PW Doppler mode or in the CW Doppler mode may be selected by an operation of the user.

The Doppler processing unit 36 sequentially performs fast Fourier transform processing on the phase-adjusted reception signal divided for a predetermined time length, sequentially generates frequency spectrum data of the Doppler shift frequency with an elapse of time, and outputs the frequency spectrum data to the Doppler image generation unit 38. Here, the Doppler shift frequency refers to a frequency representing a shift in frequency of the reception signal with respect to a frequency of the transmission signal.

The Doppler image generation unit 38 generates Doppler waveform image data based on a plurality of sets of frequency spectrum data that are sequentially output with the elapse of time. FIG. 2 shows an example of a Doppler waveform image indicated by the Doppler waveform image data. In the Doppler waveform image, time is set in a horizontal axis direction, and a Doppler shift frequency (blood flow velocity) is set in a vertical axis direction. Brightness of a plurality of images arranged in the vertical direction at a certain time point on the time axis indicates a frequency spectrum corresponding to the certain time point. A baseline 52 extending linearly in the horizontal direction indicates that the Doppler shift frequency is 0. The Doppler image generation unit 38 sequentially generates the Doppler waveform image data with the elapse of time, and outputs the Doppler waveform image data to the image processing unit 34. The image processing unit 34 generates a video signal for displaying the Doppler waveform image based on the Doppler waveform image data, and outputs the video signal to the display unit 40. The display unit 40 displays the Doppler waveform image based on the video signal.

Figure 3:
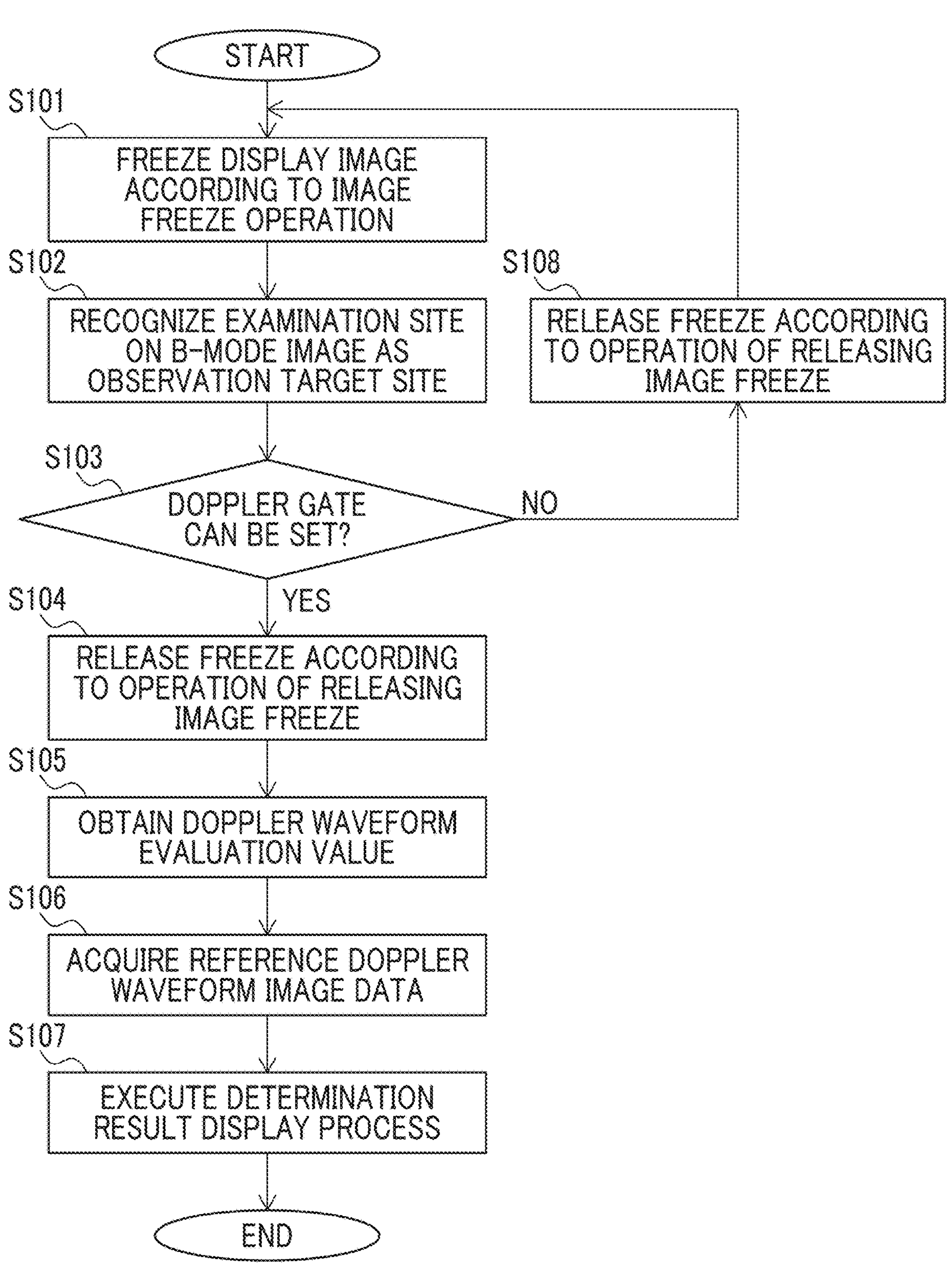
FIG. 3 is a flowchart of a Doppler waveform determination process.

The ultrasound diagnostic apparatus 100 according to the present embodiment executes a Doppler waveform determination process shown in a flowchart of FIG. 3. The Doppler waveform determination process is a process of determining how appropriate the Doppler waveform image is. The flowchart of FIG. 3 shows a process in a case where the Doppler mode is the PW Doppler mode. In the Doppler waveform determination process, an image freeze operation for freezing an image displayed on the display unit 40 is first performed by the user (S101), and B-mode image data generated immediately before the image freeze operation is a target to be processed. The B-mode image to be processed may be displayed on the display unit 40.

The image processing unit 34 recognizes an examination site such as an organ, which appears in the B-mode image, as a Doppler observation target (S102). Specifically, the image processing unit 34 executes the following process with reference to an examination site database stored in the memory 26.

The examination site database includes data for constructing an examination site specification model as a machine learning model. The examination site specification model outputs information specifying the examination site as the Doppler observation target in response to being given the B-mode image data to be processed. Here, the information specifying the examination site is, for example, character information indicating a name of the examination site or an identification (ID) predetermined for the examination site. The examination site specification model is constructed based on, for example, a plurality of sets of supervised data obtained by measurement performed in the past for a plurality of different examination sites. The supervised data may be, for example, data in which the B-mode image data to be processed and information specifying the examination site as the Doppler observation target are associated with each other. The examination site specification model may be constructed by using a machine learning algorithm such as a CNN, an AdaBoost, or an SVN. A machine learning model to be described below is also constructed by using a machine learning algorithm such as CNN, AdaBoost, or SVN. The machine learning algorithm may include a deep learning algorithm.

The examination site may be, for example, a heart, a carotid artery, a liver, a kidney, a uterus, a prostate, an upper limb, or a lower limb. A plurality of types of reference B-mode image data may be a plurality of types of image data showing tomographic images at a plurality of different positions in the examination site.

The image processing unit 34 constructs the examination site specification model by referring to the examination site database. The image processing unit 34 recognizes the Doppler observation target by obtaining the information specifying the examination site by giving the examination site specification model the B-mode image data to be processed.

The examination site database may include an examination site table in which the information specifying the examination site and a plurality of types of reference B-mode image data for the examination site are associated with each other. In this case, the image processing unit 34 may execute the following template matching process. That is, the image processing unit 34 obtains an approximation evaluation value indicating a degree of approximation between the B-mode image data to be processed and each reference B-mode image data associated with each examination site in the examination site database, and specifies reference B-mode image data having a greatest approximation evaluation value. Then, the examination site associated with the specified reference B-mode image data is recognized as the Doppler observation target appearing in the B-mode image to be processed, that is, as the Doppler observation target on the B-mode image. A degree of approximation between two image data may be a correlation value for two images indicated by the two image data.

After the Doppler observation target is recognized, the image processing unit 34 determines whether or not a Doppler gate can be set on the B-mode image based on the B-mode image data to be processed (S103). Here, the Doppler gate refers to a range on the transmission beam and the reception beam in which a blood flow velocity is measured in the Doppler mode operation, and is set in an image of a blood vessel that appears in the B-mode image. In a case where the blood vessel is recognized in the B-mode image, the image processing unit 34 determines that the Doppler gate can be set, and proceeds to step S104. In a case where the blood vessel is not recognized in the B-mode image using an image recognition technology or the like, the image processing unit 34 determines that the Doppler gate cannot be set, and proceeds to a process of step S108.

The determination as to whether or not the Doppler gate can be set may be made by the user with reference to the image displayed on the display unit 40. In this case, the process executed by the ultrasound diagnostic apparatus 100 proceeds to step S104 or step S108 according to the operation of the user.

In steps S104 and S108, the image freeze is released by performing an operation of releasing the image freeze. Alternatively, the controller 22 automatically releases the image freeze. As a result, the B-mode image data is sequentially output from the B-mode image generation unit 32 to the image processing unit 34 with the elapse of time. Further, the Doppler waveform image data is sequentially output from the Doppler image generation unit 38 to the image processing unit 34 with the elapse of time. After step S108, the process executed by the ultrasound diagnostic apparatus 100 returns to step S101.

In a case where the Doppler mode is the CW Doppler mode, steps S103 and S108 do not need to be executed.

The examination site database includes data for constructing a Doppler waveform evaluation model as a machine learning model. The Doppler waveform evaluation model outputs a Doppler waveform evaluation value and standard reference Doppler waveform image data for a blood flowing through the examination site in response to being given the information specifying the examination site and the Doppler waveform image data. The Doppler waveform evaluation value may be, for example, an evaluation value representing a degree of approximation between the reference Doppler waveform image data and the given Doppler waveform image data. The Doppler waveform evaluation model is constructed based on, for example, a plurality of sets of supervised data obtained by measurement performed in the past for a plurality of different examination sites. The supervised data may be, for example, data in which the information specifying the examination site and the Doppler waveform image data obtained for the examination site are associated with each other.

The image processing unit 34 constructs the Doppler waveform evaluation model by referring to the examination site database. The image processing unit 34 obtains the Doppler waveform evaluation value by giving the Doppler waveform evaluation model the information specifying the examination site as the Doppler observation target and the Doppler waveform image data, and acquires the reference Doppler waveform image data (S105 and S106). The image processing unit 34 executes a determination result display process described below according to the Doppler waveform evaluation value and the reference Doppler waveform image data (S107).

In a case of using the examination site table, the reference Doppler waveform image data for a blood flowing through each examination site may be associated with the information specifying each examination site, in the examination site table. In this case, after step S104 is executed, the image processing unit 34 refers to the examination site database and acquires the reference Doppler waveform image data associated with the examination site recognized as the Doppler observation target (S106). The image processing unit 34 obtains a Doppler waveform evaluation value, which is a degree of approximation between the reference Doppler waveform image data and the Doppler waveform image data output from the Doppler image generation unit 38 (S105). The image processing unit 34 executes the following determination result display process according to the Doppler waveform evaluation value (S107).

The image processing unit 34 generates determination result information indicating whether or not the Doppler waveform image data is appropriately generated. The image processing unit 34 generates a video signal for displaying the determination result information, and outputs the video signal to the display unit 40. The display unit 40 displays the determination result information based on the video signal.

The determination result information may include, for example, the following pieces of information (i) to (iii). The information included in the determination result information is not limited to (i) to (iii) below, and any other information may be included in the determination result information.

(i) A name of the examination site recognized as the Doppler observation target by the B-mode image (ii) A Doppler waveform evaluation value (iii) A Doppler waveform image acquired by the ultrasound diagnostic apparatus and a reference Doppler waveform image in the examination site recognized as the Doppler observation target The pieces of information (i) to (iii) may be sequentially updated with the elapse of time based on the Doppler waveform image data sequentially generated with the elapse of time, and may be displayed on the display unit 40 in real time. In addition, the above-described Doppler waveform evaluation value may be replaced with text representing a degree of magnitude of the Doppler waveform evaluation value, such as "large", "normal", and "small".

As described above, the information processing unit 28 provided in the ultrasound diagnostic apparatus 100 executes a process of generating the B-mode image based on transmission of the ultrasonic wave to the subject 18 and reception of the ultrasonic wave reflected by the subject 18. In addition, the information processing unit 28 executes a process of recognizing the Doppler observation target in the subject 18 on the B-mode image. This process may be a process of obtaining the information specifying the examination site as the Doppler observation target by giving the examination site specification model the B-mode image data to be processed.

The information processing unit 28 executes a process of generating the Doppler waveform image for the Doppler observation target based on transmission of the ultrasonic wave to the subject 18 and reception of the ultrasonic wave reflected by the subject 18. Further, the information processing unit 28 may obtain the Doppler waveform evaluation value by giving the Doppler waveform evaluation model the information specifying the examination site as the Doppler observation target and the Doppler waveform image generated by the Doppler image generation unit 38, and acquire the reference Doppler waveform image data.

In the ultrasound diagnostic apparatus 100 according to the present embodiment, an instruction for the operation of the ultrasound probe 14 is provided to the user by the operation unit 24 and the display unit 40 as a man-machine interface based on the Doppler waveform evaluation value. For example, in a case where the Doppler waveform evaluation value is less than a predetermined threshold value, a text, a figure, or the like prompting the user to adjust a position or a posture of the ultrasound probe 14 may be displayed. In this case, the image processing unit 34 may obtain the Doppler waveform evaluation value sequentially with the elapse of time based on the Doppler waveform image data sequentially generated with the elapse of time, and may display the instruction that changes in real time on the display unit 40. The user may refer to the Doppler waveform image and the reference Doppler waveform image displayed on the display unit 40 and adjust the position and the posture of the ultrasound probe 14.

An acceleration sensor may be provided in the ultrasound probe 14. An acceleration detection value detected by the acceleration sensor is output to the controller 22, and the Doppler waveform evaluation value is output from the image processing unit 34 to the controller 22. For example, in a case where the acceleration detection value is equal to or greater than a predetermined threshold value and the Doppler waveform evaluation value is less than a predetermined threshold value, the controller 22 outputs an instruction to stop the ultrasound probe 14 to the image processing unit 34. The image processing unit 34 displays the instruction on the display unit 40.

The instruction may be generated by the machine learning model. For example, the memory 26 stores, as the supervised data, data in which the B-mode image data, the Doppler waveform image data, the Doppler waveform evaluation value, the acceleration detection value, and the like, which are acquired in the past, are associated with each other. The controller 22 constructs an instructor as a machine learning model in the controller 22 based on the supervised data stored in the memory 26. The instructor generates an instruction including information on how to move the ultrasound probe 14 in response to being given the B-mode image data, the Doppler waveform image data, the Doppler waveform evaluation value, and the like, which are at a current time point. The controller 22 displays the instruction generated by the instructor on the display unit 40.

In general, the standard Doppler waveform image in the blood vessel that appears in the B-mode image varies depending on the examination site. Therefore, even in a case where the B-mode image and the Doppler waveform image are displayed on the display unit 40 for a certain examination site, it is difficult for the user to grasp whether or not the Doppler waveform image is appropriate, whether the position or the posture of the ultrasound probe 14 to be brought into contact with the subject 18 is appropriate, and the like. With the ultrasound diagnostic apparatus 100 according to the present embodiment, the Doppler waveform evaluation value indicates how appropriate the Doppler waveform image is. In addition, the instruction is displayed on the display unit 40, so that the user can easily grasp whether the position or the posture of the ultrasound probe 14 to be brought into contact with the subject 18 is appropriate.

In the ultrasound diagnostic apparatus 100, a disease determination result display process may be executed instead of the determination result display process (S107) or together with the determination result display process (S107). The disease determination result display process is a process of determining whether or not a disease is recognized in the subject 18 based on the Doppler waveform image data by using a machine learning model described below.

The examination site database includes data for constructing a disease determination model as the machine learning model. The disease determination model outputs a type of a disease, a disease possibility evaluation value for the disease, and disease Doppler waveform image data in response to being given the information specifying the examination site and the Doppler waveform image data. For example, in a case where the examination site is a carotid artery, the disease is a stenosis of the carotid artery. The disease Doppler waveform image data includes reference Doppler waveform image data of a position where the stenosis occurs, reference Doppler waveform image data of an upstream side of the stenosis, and reference Doppler waveform image data of a downstream side of the stenosis. The disease possibility evaluation value may be, for example, an evaluation value representing a degree of approximation between the disease Doppler waveform image data corresponding to the type of the specified disease and the given Doppler waveform image data.

Figure 4:
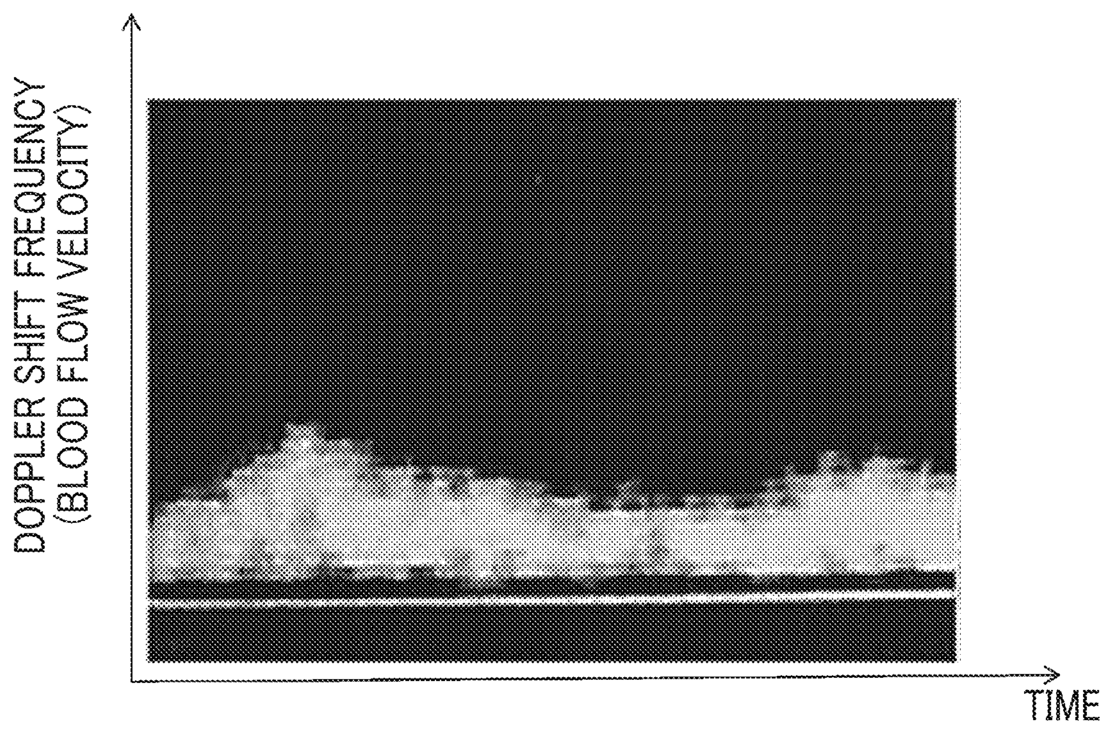
FIG. 4 is a diagram showing a Doppler waveform image of a position where a stenosis has occurred.
Figure 5:
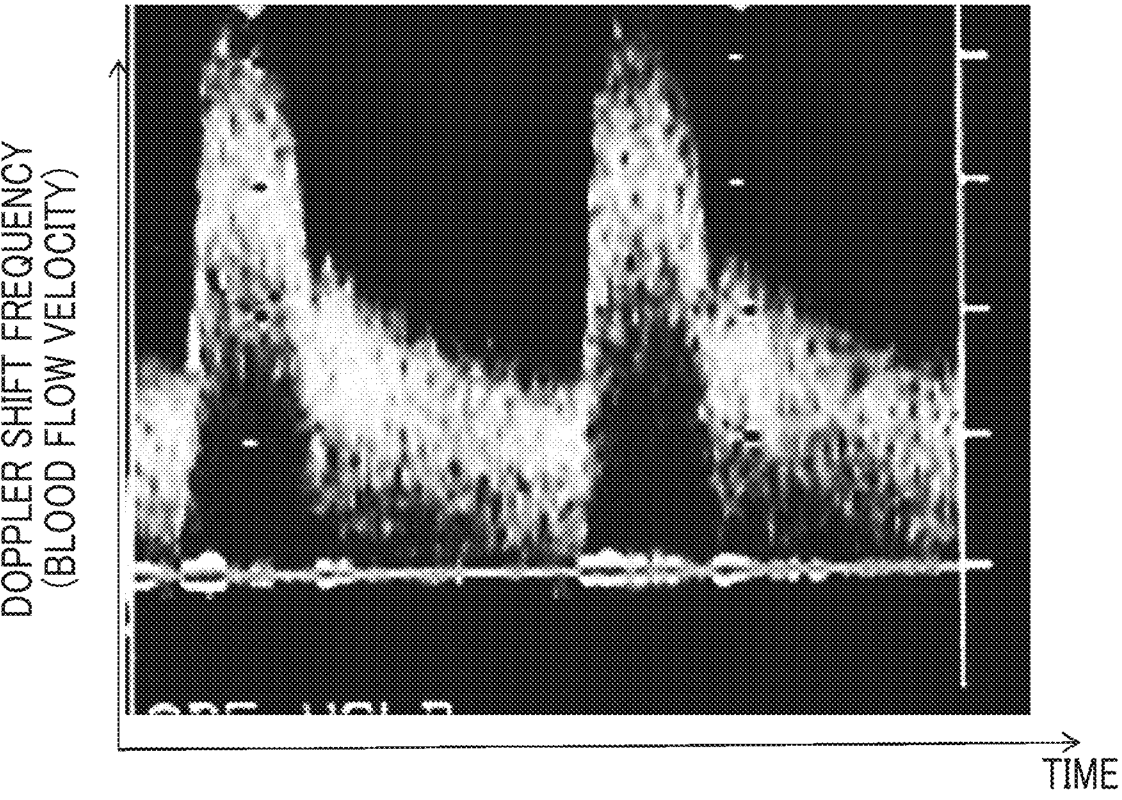
FIG. 5 is a diagram showing a Doppler waveform image of an upstream side of the stenosis.
Figure 6:
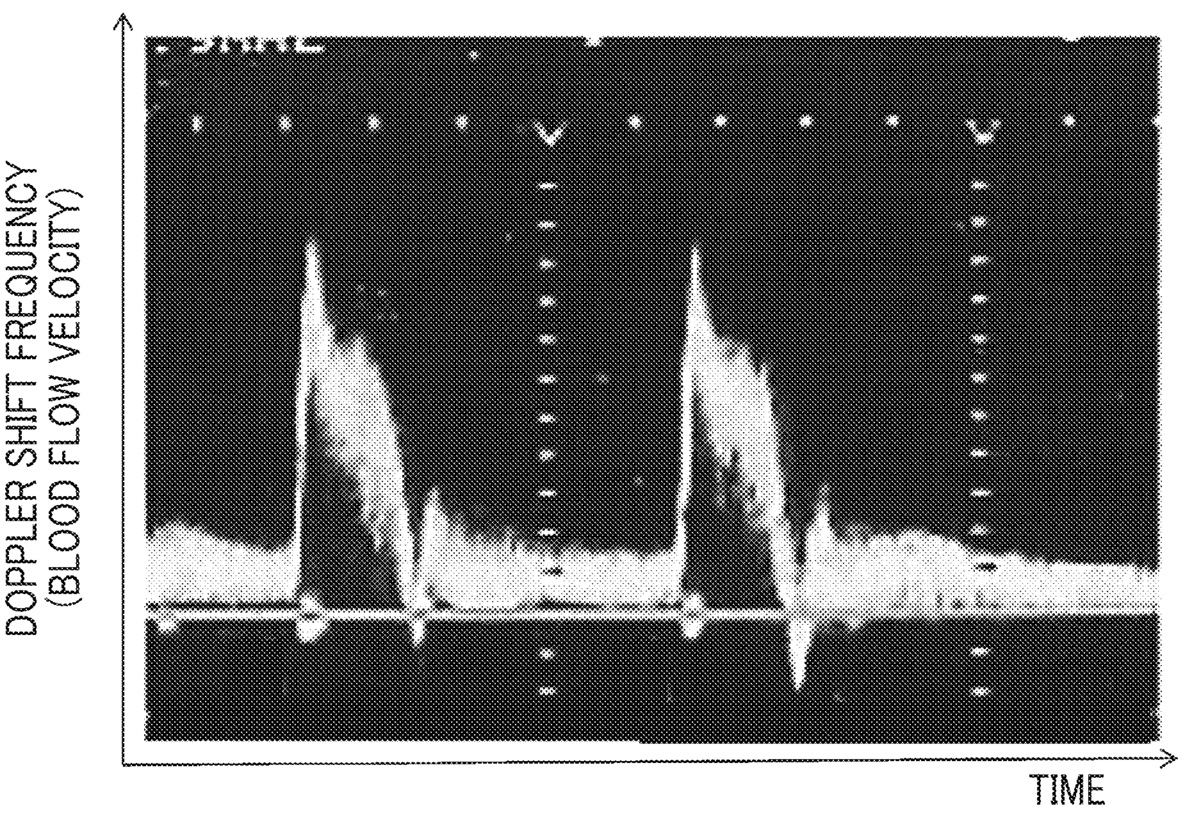
FIG. 6 is a diagram showing a Doppler waveform image of a downstream side of the stenosis.

FIG. 2 described above is a Doppler waveform image for a normal artery. FIG. 4 shows a Doppler waveform image of a position where the stenosis has occurred. FIG. 5 shows a Doppler waveform image of the upstream side of the stenosis. FIG. 6 shows a Doppler waveform image of the downstream side of the stenosis.

The disease determination model is constructed based on, for example, a plurality of sets of supervised data obtained by measurement performed in the past for a plurality of different examination sites. The supervised data may be, for example, data in which the information specifying the examination site, the information specifying the type of the disease, and the Doppler waveform image data obtained for the disease of the examination site are associated with each other.

The image processing unit 34 constructs the disease determination model by referring to the examination site database. The image processing unit 34 acquires the information specifying the type of the disease, the disease possibility evaluation value for the disease, and the disease Doppler waveform image data by giving the disease determination model the information specifying the examination site and the Doppler waveform image data.

In a case where a plurality of types of diseases are specified for the examination site recognized as the Doppler observation target, the image processing unit 34 acquires the information for specifying the type of the disease, the disease possibility evaluation value, and the disease Doppler waveform image data for each of the plurality of types of diseases. The image processing unit 34 executes the following disease determination result display process according to each acquired information, data, and the like.

In a case of using the examination site table, in the examination site table, in addition to the reference Doppler waveform image data for the blood flowing through each examination site, the disease Doppler waveform image data showing the Doppler waveform image in a case where a disease is recognized in the examination site may be associated with each examination site. In this case, the image processing unit 34 refers to the examination site database and acquires the disease Doppler waveform image data associated with the examination site recognized as the Doppler observation target. The image processing unit 34 obtains a disease possibility evaluation value indicating a degree of approximation between the disease Doppler waveform image data and the Doppler waveform image data output from the Doppler image generation unit 38.

The image processing unit 34 generates disease possibility information indicating a possibility that a disease is recognized. The image processing unit 34 generates a video signal for displaying the disease possibility information, and outputs the video signal to the display unit 40. The display unit 40 displays the disease possibility information based on the video signal.

The disease possibility information may include, for example, the following pieces of information (iv) to (vi). The information included in the disease possibility information is not limited to (iv) to (vi) below, and any other information may be included in the disease possibility information.

(iv) A name of the examination site recognized as the Doppler observation target by the B-mode image (v) A type of disease and a disease possibility evaluation value for the disease (vi) A Doppler waveform image acquired by the ultrasound diagnostic apparatus 100 and a disease Doppler waveform image for the examination site recognized as the Doppler observation target The pieces of information (i) to (vi) may be sequentially updated with the elapse of time based on the Doppler waveform image data sequentially generated with the elapse of time, and may be displayed on the display unit 40 in real time. In addition, the disease possibility evaluation value may be replaced with a text representing a degree of magnitude of the disease possibility evaluation value, such as "findings present" or "findings absent".

The examination site database includes data for constructing a detail evaluation model as the machine learning model. The detail evaluation model outputs, in response to being given the information specifying the examination site and the Doppler waveform image data, a detail included in the specified examination site, detail reference Doppler waveform image data, and a detail evaluation value. In a case where the examination site is a lower limb of the subject 18, the detail may be, for example, a peripheral blood vessel. The detail reference Doppler waveform image data is data showing a standard Doppler waveform image for the detail. The detail evaluation value indicates a degree of approximation between the detail reference Doppler waveform image data and the given Doppler waveform image data. The detail evaluation model is constructed based on, for example, a plurality of sets of supervised data obtained by measurement performed in the past for a plurality of different examination sites. The supervised data may be, for example, data in which the information specifying the examination site, the Doppler waveform image data obtained for the examination site, and the information specifying the detail included in the examination site are associated with each other.

The image processing unit 34 first recognizes the examination site as the Doppler observation target on the B-mode image, and then constructs the detail evaluation model by referring to the examination site database. The image processing unit 34 acquires the information specifying the detail, the detail reference Doppler waveform image data, and the detail evaluation value by giving the detail evaluation model the information specifying the examination site and the Doppler waveform image data.

Using the detail evaluation model, the detail included in the examination site that has been previously recognized as the Doppler observation target on the B-mode image is newly recognized as the Doppler observation target. The determination result display process for the detail recognized as the Doppler observation target and the disease determination result display process are the same as in a case where the examination site is recognized as the Doppler observation target.

In a case of using the examination site table, a plurality of types of detail reference Doppler waveform image data for the detail included in each examination site may be associated with each examination site, in the examination site table. The image processing unit 34 first recognizes the examination site as the Doppler observation target on the B-mode image, and then refers to the examination site database and acquires the detail reference Doppler waveform image data associated with the examination site recognized as the Doppler observation target. The image processing unit 34 obtains a detail evaluation value indicating a degree of approximation between the detail reference Doppler waveform image data and the Doppler waveform image data output from the Doppler image generation unit 38. The image processing unit 34 obtains the detail evaluation value by the same process for each of a plurality of detail reference Doppler waveform images. In this case, the image processing unit 34 specifies detail reference Doppler waveform image data having a greatest detail evaluation value. Then, the detail associated with the specified detail reference Doppler waveform image data is recognized as the Doppler observation target on the B-mode image. As a result, the detail included in the examination site that has been previously recognized as the Doppler observation target on the B-mode image is newly recognized as the Doppler observation target. The determination result display process for the detail recognized as the Doppler observation target and the disease determination result display process are the same as in a case where the examination site is recognized as the Doppler observation target.

The image processing unit 34 that executes the determination result display process generates determination result information indicating whether or not the Doppler waveform image data is appropriately generated. The image processing unit 34 generates a video signal for displaying the determination result information, and outputs the video signal to the display unit 40. The display unit 40 displays the determination result information based on the video signal.

The determination result information may include, for example, the following pieces of information (a) to (c).

(a) A name of the detail recognized as the Doppler observation target by the B-mode image (information specifying the detail)

(b) A detail evaluation value (c) A Doppler waveform image acquired by the ultrasound diagnostic apparatus and a reference Doppler waveform image in the examination site recognized as the Doppler observation target The image processing unit 34 that executes the disease determination result display process generates disease possibility information indicating a possibility that a disease is recognized. The image processing unit 34 generates a video signal for displaying the disease possibility information, and outputs the video signal to the display unit 40. The display unit 40 displays the disease possibility information based on the video signal.

The disease possibility information may include, for example, the following pieces of information (d) to (f).

(d) A name of the detail recognized as the Doppler observation target by the B-mode image (e) A type of disease and a disease possibility evaluation value for the disease (f) A Doppler waveform image acquired by the ultrasound diagnostic apparatus 100 and a disease Doppler waveform image for the detail recognized as the Doppler observation target As described above, the information processing unit 28 provided in the ultrasound diagnostic apparatus 100 executes the process of recognizing the detail in the Doppler observation target in the subject 18 on the B-mode image. The process may include a process of giving the detail evaluation model the information specifying the examination site and the Doppler waveform image data and acquiring the detail included in the specified examination site, the detail reference Doppler waveform image data, and the detail evaluation value.

In a case where the Doppler waveform evaluation value is less than a predetermined reference value, the image processing unit 34 may execute an auto optimizer function in the determination result display process in step S107. The auto optimizer function is a function of adjusting an operation parameter of the ultrasound diagnostic apparatus 100 based on the B-mode image data. Examples of the B-mode operation parameter include a depth of an observation range, a gain with respect to a reception signal, a time gain control (a control value for adjusting a state in which a gain is increased with an elapse of a reception time), and a focus (a degree of convergence of an ultrasonic beam). By executing the auto optimizer function, the image processing unit 34 adjusts an image quality of the B-mode image to be processed to an image quality that is easy for the user to recognize.

Further, a Doppler mode operation parameter includes repetition frequency PRF (velocity range), baseline, and the like. By executing the auto optimizer function, the image processing unit 34 traces a Doppler waveform appearing in the Doppler waveform image, and adjusts a range of the Doppler shift frequency, that is, a velocity range, a position of the baseline, and the like based on the traced Doppler waveform. The controller 22 executes the auto optimizer function, and the controller 22 adjusts operation parameters of the beam controller 10, the transmission unit 12, the reception unit 20, and the information processing unit 28.

In a case where the Doppler waveform evaluation value is less than a predetermined reference value, the determination result information may include information for prompting the user to execute the auto optimizer function. In response to display of this information, the user may perform an operation of executing the auto optimizer function. The controller 22 executes the auto optimizer function in response to the operation of the user.

In a case where the Doppler waveform evaluation value is less than a predetermined reference value, the controller 22 may execute the auto optimizer function without the operation by the user.

Configuration of Present Disclosure

Configuration 1

An ultrasound diagnostic apparatus comprising:

an information processing unit that executes

- a process of generating a B-mode image based on transmission of an ultrasonic wave to a subject and reception of the ultrasonic wave reflected by the subject,
- a process of recognizing a Doppler observation target in the subject on the B-mode image,
- a process of generating a Doppler waveform image for the Doppler observation target based on transmission of an ultrasonic wave to the subject and reception of the ultrasonic wave reflected by the subject, and
- a process of generating an evaluation value for the Doppler waveform image based on a reference Doppler waveform image corresponding to the Doppler observation target and the Doppler waveform image.

Configuration 2

The ultrasound diagnostic apparatus according to Configuration 1, in which the information processing unit constructs a machine learning model that specifies an examination site as the Doppler observation target in response to being given the B-mode image, and outputs the evaluation value for the reference Doppler waveform image in response to being given information specifying the examination site and the Doppler waveform image.

Configuration 3

The ultrasound diagnostic apparatus according to Configuration 1, in which the information processing unit executes a process of recognizing one of a plurality of types of examination sites as the Doppler observation target by referring to the B-mode image and an examination site database in which a reference B-mode image is associated with each of the plurality of types of examination sites.

Configuration 4

The ultrasound diagnostic apparatus according to Configuration 3, in which the information processing unit obtains a degree of approximation between the B-mode image and the reference B-mode image for the plurality of types of examination sites, specifies reference B-mode image data having a greatest degree of approximation, and recognizes the examination site associated with the specified reference B-mode image data as the Doppler observation target.

Configuration 5

The ultrasound diagnostic apparatus according to any one of Configurations 1 to 4, in which the information processing unit constructs a disease determination model that outputs a type of a disease, a disease possibility evaluation value for the disease, and disease Doppler waveform image data in response to being given information specifying a Doppler observation examination site and Doppler waveform image data, and sets the Doppler observation target as the Doppler observation examination site.

Configuration 6

The ultrasound diagnostic apparatus according to any one of Configurations 1 to 5, in which the information processing unit executes a process of indicating a possibility that a disease is recognized in the Doppler observation target based on a disease Doppler waveform image showing a Doppler waveform image in a case where the disease is recognized in the Doppler observation target and the Doppler waveform image.

Configuration 7

The ultrasound diagnostic apparatus according to any one of Configurations 1 to 6, in which the information processing unit

- executes a process of displaying the evaluation value, and
- executes a process of adjusting an operation parameter of the ultrasound diagnostic apparatus based on the B-mode image or the Doppler waveform image, in response to an operation of a user when the evaluation value is displayed.

Configuration 8

The ultrasound diagnostic apparatus according to any one of Configurations 1 to 7, in which the information processing unit executes a process of adjusting an operation parameter of the ultrasound diagnostic apparatus based on the B-mode image or the Doppler waveform image, in a case where the evaluation value is less than a predetermined reference value.

Configuration 9

The ultrasound diagnostic apparatus according to any one of Configurations 1 to 8, in which the information processing unit constructs a detail evaluation model that outputs a detail included in a detail observation examination site, the reference Doppler waveform image for the detail, and the evaluation value in response to being given information specifying the detail observation examination site and the Doppler waveform image, and sets the Doppler observation target for which the evaluation value has been previously generated as the detail observation examination site in the detail evaluation model.

Configuration 10

The ultrasound diagnostic apparatus according to any one of Configurations 1 to 8, in which the information processing unit executes a process of recognizing a detail included in the Doppler observation target for which the evaluation value has been previously generated based on the Doppler waveform image and the reference Doppler waveform image for a detail included in an examination site, and the process of generating the evaluation value includes a process of generating the evaluation value based on the Doppler waveform image and the reference Doppler waveform image corresponding to the detail.

Configuration 11

The ultrasound diagnostic apparatus according to any one of Configurations 1 to 10, in which the information processing unit executes a process of providing a user with an instruction for an operation of an ultrasound probe through a man-machine interface based on the evaluation value.

What is claimed is:

1. An ultrasound diagnostic apparatus comprising:

one or more processors that are configured to execute a process of generating a B-mode image based on transmission of a first ultrasonic wave to a subject and reception of the first ultrasonic wave reflected by the subject, a process of recognizing a Doppler observation target in the subject on the B-mode image, a process of generating a Doppler waveform image for the Doppler observation target based on transmission of a second ultrasonic wave to the subject and reception of the second ultrasonic wave reflected by the subject, and a process of generating a first evaluation value for the Doppler waveform image based on a reference Doppler waveform image corresponding to the Doppler observation target and the Doppler waveform image, wherein the one or more processors are further configured to execute a process of freezing an image to be displayed and using the B-mode image generated immediately before an image freeze operation for recognizing the Doppler observation target, and a process of releasing the image freezing in response to the Doppler observation target being recognized.

2. The ultrasound diagnostic apparatus according to claim 1, wherein the one or more processors are configured to construct a machine learning model that is configured to specify an examination site as the Doppler observation target in response to being given the B-mode image, and are configured to output a second evaluation value for the reference Doppler waveform image in response to being given information specifying the examination site and the Doppler waveform image.

3. The ultrasound diagnostic apparatus according to claim 1, wherein the one or more processors are configured to construct a disease determination model that outputs a type of a disease, a disease possibility evaluation value for the disease, and disease Doppler waveform image data in response to being given information specifying an examination site and Doppler waveform image data, and set the Doppler observation target as the examination site.

4. The ultrasound diagnostic apparatus according to claim 1, wherein the one or more processors are configured to execute a process of indicating a possibility that a disease is recognized in the Doppler observation target based on a disease Doppler waveform image showing the Doppler waveform image in a case where the disease is recognized in the Doppler observation target and the Doppler waveform image.

5. The ultrasound diagnostic apparatus according to claim 1, wherein the one or more processors are configured to execute a process of displaying the first evaluation value, and execute a process of adjusting an operation parameter of the ultrasound diagnostic apparatus based on the B-mode image or the Doppler waveform image, in response to an operation of a user when the first evaluation value is displayed.

6. The ultrasound diagnostic apparatus according to claim 1, wherein the one or more processors are configured to execute a process of adjusting an operation parameter of the ultrasound diagnostic apparatus based on the B-mode image or the Doppler waveform image, in a case where the first evaluation value is less than a predetermined reference value.

7. The ultrasound diagnostic apparatus according to claim 1, wherein the one or more processors are configured to construct a detail evaluation model that is configured to output a detail included in an examination site, the reference Doppler waveform image for the detail, and the first evaluation value in response to being given information specifying the examination site and the Doppler waveform image, and set the Doppler observation target for which the first evaluation value has been previously generated as the examination site in the detail evaluation model.

8. The ultrasound diagnostic apparatus according to claim 1, wherein the one or more processors are configured to execute a process of recognizing a detail included in the Doppler observation target for which the first evaluation value has been previously generated based on the Doppler waveform image and the reference Doppler waveform image for a detail included in an examination site, and the process of generating the first evaluation value includes a process of generating the first evaluation value based on the Doppler waveform image and the reference Doppler waveform image corresponding to the detail.

9. The ultrasound diagnostic apparatus according to claim 1, wherein the one or more processors are configured to execute a process of providing a user with an instruction for an operation of an ultrasound probe through a man-machine interface based on the first evaluation value.

10. The ultrasound diagnostic apparatus according to claim 1, wherein the one or more processors are configured to execute a process of recognizing one of a plurality of types of examination sites as the Doppler observation target by referring to the B-mode image and an examination site database in which a reference B-mode image is associated with each of the plurality of types of examination sites.

11. The ultrasound diagnostic apparatus according to claim 10, wherein the one or more processors are configured to obtain a degree of approximation between the B-mode image and the reference B-mode image for the plurality of types of examination sites, specify reference B-mode image having a greatest degree of approximation, and recognize the examination site associated with the specified reference B-mode image as the Doppler observation target.

* * * * *